(12) United States Patent
John et al.

(10) Patent No.: US 7,348,314 B2
(45) Date of Patent: Mar. 25, 2008

(54) COMPOSITIONS AND METHODS FOR INHIBITING VIRAL REPLICATION

(75) Inventors: Matthias John, Hallstadt (DE); Stefan Limmer, Neudrossenfeld (DE); Hans-Peter Vornlocher, Bayreuth (DE); Roland Kreutzer, Weidenberg (DE)

(73) Assignee: Alnylam Europe AG, Kulmbach (DE)

( * ) Notice: Subject to any disclaimer, the term of this patent is extended or adjusted under 35 U.S.C. 154(b) by 489 days.

(21) Appl. No.: 10/384,512

(22) Filed: Mar. 7, 2003

(65) Prior Publication Data

US 2004/0091457 A1 May 13, 2004

Related U.S. Application Data

(63) Continuation-in-part of application No. PCT/EP02/11432, filed on Oct. 11, 2002.

(30) Foreign Application Priority Data

| Oct. 12, 2001 | (DE) | ................. 101 50 187 |
| Oct. 26, 2001 | (DE) | ................. 101 55 280 |
| Nov. 29, 2001 | (DE) | ................. 101 58 411 |
| Dec. 7, 2001 | (DE) | ................. 101 60 151 |
| Dec. 20, 2001 | (DE) | ................. 101 63 098 |

(51) Int. Cl.
*A61K 31/70* (2006.01)
*C07H 21/04* (2006.01)
*C07H 21/00* (2006.01)

(52) U.S. Cl. .................. 514/44; 536/24.5; 536/25.3

(58) Field of Classification Search .................. None
See application file for complete search history.

(56) References Cited

U.S. PATENT DOCUMENTS

| 6,423,489 B1 | 7/2002 | Anderson et al. ............ 435/6 |
| 6,486,299 B1 | 11/2002 | Skimkets .................. 530/350 |
| 6,506,559 B1 | 1/2003 | Fire et al. .................. 435/6 |
| 2002/0086356 A1 | 7/2002 | Tuschl et al. ............ 435/69.1 |
| 2002/0114784 A1 | 8/2002 | Li et al. .................. 424/93.2 |
| 2002/0123034 A1 | 9/2002 | Canaani et al. .............. 435/4 |
| 2002/0132346 A1 | 9/2002 | Cibelli .................... 435/455 |
| 2002/0162126 A1 | 10/2002 | Beach et al. .................. 800/8 |
| 2002/0173478 A1 | 11/2002 | Gerwitz .................... 514/44 |
| 2003/0027783 A1 | 2/2003 | Zernicka-Goetz et al. .... 514/44 |
| 2003/0108923 A1 | 6/2003 | Tuschl et al. ................ 435/6 |
| 2003/0125281 A1 | 7/2003 | Lewis et al. ............... 514/44 |
| 2003/0143732 A1 | 7/2003 | Fosnaugh et al. ........... 435/325 |
| 2003/0148341 A1 | 8/2003 | Sin et al. ..................... 435/6 |
| 2003/0157030 A1 | 8/2003 | Davis et al. .................. 424/46 |
| 2003/0176671 A1 | 9/2003 | Reed et al. ................ 536/23.1 |
| 2003/0180756 A1 | 9/2003 | Shi et al. ...................... 435/6 |
| 2003/0190635 A1 | 10/2003 | McSwiggen .................. 435/6 |
| 2003/0198627 A1 | 10/2003 | Arts et al. ................ 424/93.21 |

FOREIGN PATENT DOCUMENTS

| WO | WO 99/32619 | 7/1999 |
| WO | WO 99/53050 | 10/1999 |
| WO | WO 99/61631 | 12/1999 |
| WO | WO 00/01846 | 1/2000 |
| WO | WO 00/44895 | 8/2000 |
| WO | WO 00/44914 | 8/2000 |
| WO | WO 00/63364 | 10/2000 |
| WO | WO 00/68374 | 11/2000 |
| WO | WO 01/18197 A1 | 3/2001 |
| WO | WO 01/29058 A1 | 4/2001 |
| WO | WO 01/36646 A1 | 5/2001 |
| WO | WO 01/42443 A1 | 6/2001 |
| WO | WO 01/48183 A2 | 7/2001 |
| WO | WO 01/68836 A2 | 9/2001 |
| WO | WO 01/70949 A1 | 9/2001 |
| WO | WO 01/75164 A2 | 10/2001 |
| WO | WO 01/92513 A1 | 12/2001 |
| WO | WO 02/16620 A2 | 2/2002 |
| WO | WO 02/26780 A2 | 4/2002 |
| WO | WO 02/44321 A2 | 6/2002 |
| WO | WO 02/055692 A2 | 7/2002 |
| WO | WO 02/055693 A2 | 7/2002 |
| WO | WO 02/061034 A2 | 8/2002 |
| WO | WO 03/006477 A1 | 8/2002 |
| WO | WO 02/068635 A2 | 9/2002 |
| WO | WO 02/068637 A2 | 9/2002 |
| WO | WO 03/012052 A2 | 2/2003 |
| WO | WO 03/012082 A2 | 2/2003 |

(Continued)

OTHER PUBLICATIONS

Ito et al. Journal of Virology 1998, vol. 72, pp. 8789-8796.*

(Continued)

*Primary Examiner*—Richard Schnizer
*Assistant Examiner*—Tracy Vivlemore
(74) *Attorney, Agent, or Firm*—Lowrie, Lando & Anastasi, LLP

(57) ABSTRACT

The present invention relates to a double-stranded ribonucleic acid (dsRNA) having a nucleotide sequence which is less that 30 nucleotides in length and which is substantially identical to at least a part of a 3'-untranslated region (3'-UTR) of a (+) strand RNA virus, such as HCV, as well as pharmaceutical compositions comprising the dsRNA, together with a pharmaceutically acceptable carrier. The pharmaceutical compositions are useful for treating infections and diseases caused by the replication or activity of the (+) strand RNA virus, as well as methods for inhibiting viral replication.

3 Claims, 6 Drawing Sheets

FOREIGN PATENT DOCUMENTS

| | | |
|---|---|---|
| WO | WO 03/016572 A1 | 2/2003 |
| WO | WO 03/033700 A1 | 4/2003 |
| WO | WO 03/035082 A1 | 5/2003 |
| WO | WO 03/035083 A1 | 5/2003 |
| WO | WO 03/035868 A1 | 5/2003 |
| WO | WO 03/035869 A1 | 5/2003 |
| WO | WO 03/035870 A1 | 5/2003 |
| WO | WO 03/035876 A1 | 5/2003 |
| WO | WO 03/070750 A2 | 8/2003 |
| WO | WO 03/070969 A2 | 8/2003 |
| WO | WO 03/070972 A2 | 8/2003 |
| WO | WO 03/070283 A2 | 9/2003 |
| WO | WO 03/074654 A2 | 9/2003 |
| WO | WO 03/080794 A2 | 10/2003 |
| WO | WO 03/080807 A2 | 10/2003 |

OTHER PUBLICATIONS

Jackson et al. Nature Biotechnology 2003 vol. 21, pp. 635-637.*

Hamada et al. Antisense and Nucleic Acid Drug Development 2002, vol. 12, pp. 301-309.*

Holen, T. et al., (2002), "Positional effects of short interfering RNAs targeting the human coagulation trigger Tissue Factor", *Nucleic Acids Research*, 30(8):1757-1766.

Ambros, V., (2001), "Dicing Up RNAs", *Science*, 293:811-813.

Elbashir, S.M. et al., (2001), "Duplexes of 21-nucleotide RNAs mediate RNA interference in cultured mammalian cells", *Nature*, 411:494-498.

Gautschi, O. et al., (2001), "Actvity of a Novel bcl-2/bcl-xL-Bispecific Antisense Oligonucleotide Against Tumors of Diverse Histologic Origins", *Journal of the National Cancer Institute*, 93(6):463-471.

Lipardi, C. et al., (2001), "RNAi as Random Degradative PCR: siRNA Primers Convert mRNA into dsRNAs that Are Degraded to Generate New siRNAs", *Cell*, 107:297-307.

Sharp, P.A., (2001), "RNA interference—2001", *Genes & Development*, 15:485-490.

Sijen, T. et al., (2001), "On the Role of RNA Amplification in dsRNA-Triggered Gene Silencing", *Cell*, 107:465-476.

Bass, B.L., (2000), "Double-Stranded RNA as a Template for Gene Silencing", *Cell*, 101:235-238.

Cobaleda, C. et al., (2000), "In vivo inhibition by a site-specific catalytic RNA subunit of Rnase P designed against the BCR-ABL oncogenic products: a novel approach for cancer treatment", *Blood*, 95(3):731-737.

Hammond, S.M. et al., (2000), "An RNA-directed nuclease mediates post-transcriptional gene silencing in *Drosophila* cells", *Nature*, 404:293-296.

Yang, D. et al., (2000), "Evidence that processed small dsRNAs may mediate sequence-specific mRNA degradation during RNAi in *Drosophila* embryos", *Current Biology*, 10:1191-1200.

Wianny, F. et al., (2000), "Specific interference with gene function by double-stranded RNA in early mouse development", *Nature Cell Biology*, 2:70-75.

Zamore, P.D. et al., (2000), "RNAi: Double-Stranded RNA Directs the ATP-Dependent Cleavage of mRNA at 21 to 23 Nucleotide Intervals", *Cell*, 101:25-33.

Fire, A., (1999), "RNA-triggered gene silencing", *TIG*, 15(9):358-363.

Tuschl, T. et al., (1999), "Targeted mRNA degradation by double-stranded RNA in vitro", *Genes & Development*, 13:3191-3197.

Wild, K. et al., (1999), "The 2 Å structure of helix 6 of the human signal recognition particle RNA", *Structure*, 7(11):1345-1352.

Caplen, N.J., (2002), "A new approach to the inhibition of gene expression", *TRENDS in Biotechnology*, 20(2):49-51.

Caplen, N.J. et al., (2001), "Specific inhibition of gene expression by small double-stranded RNAs in invertebrate and vertebrate systems", *Proc. Natl. Acad. Sci. USA*, 98(17):9742-9747.

Doench, J.G. et al., (2003), "siRNAs can function as miRNAs", *Genes & Development*, 17:438-442.

Donzé, O. et al., (2002), "RNA interference in mammalian cells using siRNAs synthesized with T7 RNA Polymerase", *Nucleic Acids Research*, 30(10):e46(4pages).

Elbashir, S.M. et al., (2001), "RNA interference is mediated by 21- and 22-nucleotide RNAs", *Genes & Development*, 15:188-200.

Elbashir, S.M. et al., (2001), "Functional anatomy of siRNAs for mediating efficient RNAi in *Drosophila melanogaster* embryo lysate", *The EMBO Journal*, 20(23):6877-6888.

Fire, A. et al., (1998), "Potent and specific genetic interference by double-stranded RNA in *Caenorhabditis elegans*", *Nature*, 391:806-811.

Harborth, J. et al., (2001), "Identification of essential genes in cultured mammalian cells using small interfering RNAs", *Journal of Cell Science*, 114(24):4557-4565.

Lewis, D.L. et al., (2002), "Efficient delivery of siRNA for inhibition of gene expression in postnatal mice", *Nature Genetics*, 32:107-108.

Manche, L. et al., (1992), "Interactions between Double-Stranded RNA Regulators and the Protein Kinase DAI", *Molecular and Cellular Biology*, 12(11):5238-5248.

McCaffrey, A.P. et al., (2002), "RNA interference in adult mice", *Nature*, 418:38-39.

Ngô, H. et al., (1998), "Double-stranded RNA induces mRNA degradation in *Trypanosoma brucei*", *Proc. Natl. Acad. Sci.*, 95:14687-14692.

Paddison, P.J. et al., (2002), "Short hairpin RNAs (shRNAs) induce sequence-specific silencing in mammalian cells", *Genes & Development*, 16:948-958.

Randall, G. et al., (2003), "Clearance of replicating hepatitis C virus replicon RNAs in cell culture by small interfering RNAs", *PNAS*, 100(1):235-240.

Tijsterman, M. et al., (2002), "The Genetics of RNA Silencing", *Annu. Rev. Genet.*, 36:489-519.

Yu, J. et al., (2002), "RNA interference by expression of short-interfering RNAs and hairpin RNAs in mammalian cells", *PNAS*, 99(9):6047-6052.

Wang, et al., "Specific Inhibition of Coxsackie Virus B3 Translation and Replication by Phosphorothioate Antisense Oligodeoxynucleotides", Antimicrobial Agents and Chemotherapy (USA), Apr. 2001, V. 24, No. 4, pp. 1043-1052.

Strickland, S., et al., "Antisense RNA Directed Against The 3' Noncoding Region Prevents Dormant MRNA Activation in Mouse Oocytes", Science, American Association for the Advancement of Science (USA), V. 241, 1988, pp. 680-684.

Jacque Jean-Marc, et al., "Modulation of HIV-1 Replication by RNA Interference", Nature (England), Jul. 25, 2002, V. 418, No. 6869, pp. 435-438.

International Preliminary Examination Report (PCT/EP2002/011432).

Montgomery, M.K. et al., (1998), "Double-stranded RNA as a mediator in sequence-specific genetic silencing and co-suppression", *TIG*, 14(7):255-258.

Lowy, D.R. et al., (1993), "Function and Regulation of RAS", *Annu. Rev. Biochem.*, 62:851-891.

Downward, J. et al., (1990), "Identification of a nucleotide exchange-promoting activity for p21$^{ras}$", *Proc. Natl. Acad. Sci. USA*, 87:5998-6002.

Gibbs, J.B. et al., (1988), "Purification of ras GTPase activating protein from bovine brain", *Proc. Natl. Acad. Sci. USA*, 85:5026-5030.

International Search Report of International Application No. PCT/EP02/00151, 2002.

* cited by examiner

GTC ACC ATG TCG TCA CGG CTA GCT GTG AAA GGT CCA GTC ACC ATG TCG TTT ACT TTG
 M   T   M   S   S   R   L   A   V   K   G   P   V   T   M   S   F   T   L

FIG. 1

GTC ACC TTG TCG TCA CGG CTA GCT GTG AAA GGT CCA GTC ACC ATG TCG TTT ACT TTG
 M   S   F   T   L

```
5'  uc GUC ACG GCU AGC UGU GAA AGG UCC ag    3'  mRNA p2 & p3

5'      ACG GCU AGC UGU GAA AGG UCC GU       3'  Sense Strand (HCV 1)
3'   AG UGC CGA UCG ACA CUU UCC AGG          5'  Antisense Strand (HCV 2)
```

FIG. 4

```
5'  cg GUG AAA UUA UCG AUG AGC GUG gu        3'  mRNA

5'     GUG AAA UUA UCG AUG AGC GUG gu        3'  Sense Strand (Gal 1)
3'  gc CAC UUU AAU AGC UAC UCG CAC           5'  Antisense Strand (Gal 2)
```

FIG. 5

```
5'  AGA CAG UCG ACU UCA GCC Ugg              3'  Sense Strand (HCV 3)
3'  gg UCU GUC AGC UGA AGU CGG A             5'  Antisense Strand (HCV 4)
```

FIG. 6

5' GAU GAG GAU CGU UUC GCA UGA UUG 3'  Sense Strand (K18 s)
3' UC CUA CUC CUA GCA AAG CGU ACU A 5'  Antisense Strand (K17 as)

FIG. 7

5' uc GUC ACG GCU AGC UGU GAA AGG UCC ag 3'  mRNA p3 (HCV Sequence)
3'     TGC CGA TCG ACA CTT TCC AGG       5'  HCVPTO1
3' CAG TGC CGA TCG ACA CTT TCC           5'  HCVPTO2
3' GGA CCT TTC ACA GCT AGC CGT           5'  HCVPTO3

US 7,348,314 B2

COMPOSITIONS AND METHODS FOR INHIBITING VIRAL REPLICATION

RELATED APPLICATIONS

This application is a continuation-in-part of International Application No. PCT/EP02/11432, which designated the United States and was filed on Oct. 11, 2002, which claims the benefit of German Patent No. 101 50 187.0, filed on Oct. 12, 2001, German Patent No. 101 55 280.7, filed on Oct. 26, 2001, German Patent No. 101 58 411.3, filed on Nov. 29, 2001, German Patent No. 101 60 151.4, filed on Dec. 7, 2001, German Patent No. 101 63 098.0, filed on Dec. 20, 2001, EP Patent No. PCT/EP02/00151, filed on Jan. 9, 2002, and EP Patent No. PCT/EP02/00152, filed on Jan. 9, 2002. The entire teachings of the above application(s) are incorporated herein by reference.

FIELD OF THE INVENTION

This invention relates to double-stranded ribonucleic acid (dsRNA), and its use for inhibiting the replication of (+) strand RNA viruses, such as Hepatitis C virus, as well as treating viral-associated diseases.

BACKGROUND OF THE INVENTION

Positive or plus-strand RNA viruses share many similarities in genomic organization and structure, most notably a single-stranded coding RNA of positive polarity. Representative (+) strand RNA viruses include the picornaviruses, flaviviruses, togaviruses, coronaviruses, and caliciviruses. One clinically significant representative of the flavivirus family is the hepatitis C virus (HCV), the causative agent for hepatitis C. Hepatitis C is an often chronic inflammatory disease of the liver which typically results in fibrosis and liver cancer (Choo, et al., Science (1989) 244:359). Infection by HCV typically results from contact with contaminated blood or blood products.

During HCV replication, a replicative (minus) RNA strand is produced which serves as a template for generation of several coding (+) RNA strands. The HCV genome, which contains approximately 9600 nucleotides, is translated into a polyprotein consisting of approximately 3000 amino acids (Leinbach, et al., Virology (1994) 204:163-169; Kato, et al., FEBS Letters (1991) 280:325-328). This polyprotein subsequently undergoes post-translational cleavage, producing several proteins. Due to high genetic variability and mutation rates, the HCV comprises several distinct HCV genotypes that share approximately 70% sequence identity (Simmonds, et al., J. Gen. Virol., (1994) 75:1053-1061). Despite this hypervariability, there are three regions of the HCV genome that are highly conserved, including the 5'- and 3'-non-coding regions, known as the 5'-untranslated region (5'-UTR) and 3'-untranslated region (3'-UTR), respectively. These regions are thought to be vital for HCV RNA replication as well as translation of the HCV polyprotein. In general, treatment of HCV is complicated by its high mutation rate, as well as the mode of transmission and possibility of simultaneous infection with multiple HCV genotypes.

Hepatitis C has several clinical phases. The first phase (i.e., acute phase) begins with infection by HCV. During this early phase, it is possible to detect HCV-RNA in the serum of patients using polymerase chain reaction (PCR). However, because only about 25% of patients exhibit jaundice during this phase, most cases (75%) go undetected in the early stages. The inflammatory process, characterized by an increase in serum liver enzyme concentrations, begins approximately four weeks post infection. Although acute HCV infection is not malignant, the majority of patients (approximately 80%) develop chronic liver disease, characterized by a permanent elevation in the serum alanine aminotransferase level. Cirrhosis of the liver develops in more than 20% of patients with chronic HCV disease, which frequently leads to malignant hepatoma. Life expectancy following diagnosis of the malignant hepatoma is generally 12 months.

Current therapies to treat HCV infections have met with limited success, with only a minority of patients experiencing long-term improvement. The most prevalent treatment today involves specific cytokines known as interferons, particularly interferon-α (IFN-alpha) which reduces serum alanine aminotransferase levels in approximately 50% of patients. Unfortunately, serum levels of alanine aminotransferase usually return to elevated levels following termination of treatment, producing a number of adverse side effects (Dusheiko, et al., J Viral Hepatitis (1994) 1:3). Despite these problems, IFN-alpha is commonly used to reduce the risk of cirrhosis of the liver and malignant hepatoma. There is no currently available vaccine for HCV.

Although IFN-alpha remains the conventional approach, virologists have evaluated a number of potential alternative therapies, including the use of specific ribozymes to inhibit translation of viral protein. Welch et al. disclose a two vector-expressed hairpin ribozyme directed against HCV (Welch, et al., Gene Therapy (1996), 3(11):994). Lieber et al. report the removal of HCV-RNA in infected human hepatocytes through adenovirus-mediated expression of specific hammerhead ribozymes (Lieber, et al., Virology (1996), 70 (12):8782). WO 99/55847 report the degradation of 5'- and 3'-UTL regions of HCV-RNA, as well as the 5'-coding region for the nucleoprotein, using ribozymes. U.S. Pat. No. 5,610,054 discloses enzymatic nucleic acid molecules that can inhibit replication of HCV. Despite these efforts, the therapeutic value of ribozymes for treating HCV infections remains questionable, particularly in view of their low enzymatic activity.

More recently, double-stranded RNA molecules (dsRNA) have been shown to block gene expression in a highly conserved regulatory mechanism known as RNA interference (RNAi). Briefly, the RNAse III Dicer processes dsRNA into small interfering RNAs (siRNA) of approximately 22 nucleotides, which serve as guide sequences to induce target-specific mRNA cleavage by an RNA-induced silencing complex RISC (Hammond, S. M., et al., Nature (2000), 404:293-296). When administered to a cell or organism, exogenous dsRNA has been shown to direct the sequence-specific degradation of endogenous messenger RNA (mRNA) through RNAi. WO 99/32619 (Fires et al.) discloses the use of a dsRNA of at least 25 nucleotides in length to inhibit the expression of a target gene in C. elegans. dsRNA has also been shown to degrade target RNA in other organisms, including plants (see, e.g., WO 99/53050, Waterhouse et al.; and WO 99/61631, Heifetz et al.); Drosophilia (see, e.g., Yang, D., et al., Curr. Biol. (2000) 10:1191-1200); and mammals (WO 00/44895, Limmer).

Despite significant advances in the field, there remains a need for an agent that can inhibit the replication of a virus in a host cell using the cell's own RNAi machinery. More specifically, an agent that has high biological activity and can provide long-term, effective inhibition of viral replication at a low dose, would be highly desirable. Compositions comprising such agents would be useful for treating a variety of viral infections, including HCV.

SUMMARY OF THE INVENTION

The present invention discloses double-stranded ribonucleic acid (dsRNA), as well as compositions and methods for inhibiting the replication of a (+) strand RNA virus, such as a Hepatitis C Virus (HCV). In particular, the invention relates to a dsRNA having an RNA strand (the complementary strand) comprising a region which is complementary to at least a portion of a 3'-untranslated region (3'-UTR) of a (+) strand RNA virus. The present invention also discloses compositions and methods for treating hepatitis C or HCV-associated diseases.

In one aspect, the invention relates to a dsRNA. The dsRNA comprises a sense RNA strand comprising a nucleotide sequence which is substantially identical to at least a part of a 3'-untranslated region (3'-UTR) of a (+) strand RNA virus, and the dsRNA is less than 30 nucleotides in length. The (+) strand RNA may be a hepatitis C virus. The dsRNA may further comprise a complementary RNA strand, wherein the complementary RNA strand comprises a complementary nucleotide sequence which is less than 30 nucleotides in length and is complementary to at least a portion of the 3'-UTR of the virus. In a preferred embodiment, the nucleotide sequence is within a highly conserved region of the 3'-UTR. The complementary nucleotide sequence is preferably less than 25 nucleotides in length, more preferably 21 to 24 nucleotides in length, and most preferably 23 nucleotides in length. The dsRNA may comprise one or two blunt ends. The complementary RNA strand and the sense RNA strand may comprise a 3'-terminus and a 5'-terminus, and at least one of the RNA strands may comprise a nucleotide overhang of 1 to 3 nucleotides in length, preferably two nucleotides in length. The dsRNA may further comprise two ends, wherein one end comprises the 3'-terminus of the complementary RNA strand and the 5'-terminus of the sense RNA strand, and the other end comprises the 5'-terminus of the complementary RNA strand and the 3'-terminus of the sense RNA strand. In one embodiment, one end of the dsRNA end has a nucleotide overhang, preferably on the 3'-terminus of the complementary RNA strand, and the second end is blunt. In another embodiment, the complementary RNA strand is 24 nucleotides in length and the sense RNA strand is 22 nucleotides in length, the 3'-end of the complementary RNA strand has a 2-nucleotide overhang, and the other end of the dsRNA is blunt. In a particular embodiment, the complementary RNA strand comprises the nucleotide sequence of SEQ ID NO:5 and the sense RNA strand comprises the nucleotide sequence of SEQ ID NO:4.

In another aspect, the invention relates to a pharmaceutical composition for inhibiting the replication of a (+) strand RNA virus in an organism, such as a mammal (e.g., human). The pharmaceutical composition comprises the dsRNA as described above, together with a pharmaceutically acceptable carrier. The dosage unit of dsRNA in the composition may be less than 5 milligram (mg) of dsRNA per kg body weight, preferably 0.01 to 2.5 milligrams (mg), more preferably 0.1 to 200 micrograms (μg), and most preferably 0.1 to 100 μg per kilogram body weight. In one embodiment, the pharmaceutically acceptable carrier is an aqueous solution, such as phosphate buffered saline. In another embodiment, the pharmaceutically acceptable carrier comprises a micellar structure, such a liposome, capsid, capsoid, polymeric nanocapsule, or polymeric microcapsule. The pharmaceutical composition may be formulated to be administered by inhalation, infusion, injection, or orally. In one embodiment, the pharmaceutical compositions is formulated to be administered by intravenous or intraperitoneal injection.

In yet another aspect, the invention relates to a method for inhibiting the replication of a (+) strand RNA virus comprising a 3'-untranslated region (3'-UTR) in a cell. The method comprises introducing a double-stranded ribonucleic acid (dsRNA), as described above, into the cell. The dsRNA comprises a nucleotide sequence which is substantially identical to at least a part of the 3'-UTR, and the dsRNA is less than 30 nucleotides in length, more preferably less than 25 nucleotides, more preferably 21 to 24 nucleotides, and most preferably 23 nucleotides in length.

In still another aspect, the invention relates to a method for treating a disease associated with infection of a (+) strand RNA virus in an organism. The method comprises administering a pharmaceutical composition to the organism, wherein the pharmaceutical composition comprises a double-stranded ribonucleic acid (dsRNA), as described above, together with a pharmaceutically acceptable carrier. The dsRNA comprises a nucleotide sequence which is substantially identical to at least a part of the 3'-UTR of the (+) strand RNA virus, and the dsRNA is less than 30 nucleotides in length.

The details of once or more embodiments of the invention are set forth in the accompanying drawings and the description below. Other features, objects, and advantages of the invention will be apparent from the description and drawings, and from the claims.

BRIEF DESCRIPTION OF THE FIGURES

FIG. 1 shows the relevant sequence region (SEQ ID NO: 2) from the p2 plasmid and the N-terminal amino acid sequence (SEQ ID NO:17) of the corresponding reporter protein.

FIG. 2 shows the relevant sequence region (SEQ ID NO: 3) from the p3 plasmid and the N-terminal amino acid sequence (SEQ ID NO:18) of the corresponding reporter protein.

FIG. 3 shows the HCV1-2 dsRNA (SEQ ID NO 4, SEQ ID NO 5) in contrast to the HCV sequence of an mRNA (SEQ ID NO 15) formed by means of the p2 and p3 plasmids.

FIG. 4 shows the GAL1-2 dsRNA (SEQ ID NO 6, SEQ ID NO 7) in contrast to the mRNA sequence (SEQ ID NO 16) corresponding to β-gal gene (positive control).

FIG. 5 shows the HCV3-4 the dsRNA(SEQ ID NO 8, SEQ ID NO 9), that exhibits no relation to the expressed genes (negative control).

FIG. 6 shows the K22 dsRNA (SEQ ID NO 10, SEQ ID NO 11), that exhibits no relation to the expressed genes (negative control).

FIG. 7 shows the antisense oligonucleotides HCVPT01 (SEQ ID NO 12), HCVPTO2 (SEQ ID NO 13), and HCVPTO3 (SEQ ID NO 14), in comparison to the HCV sequence of mRNA (SEQ ID NO 15) formed by the p3 plasmid.

Figure 8:
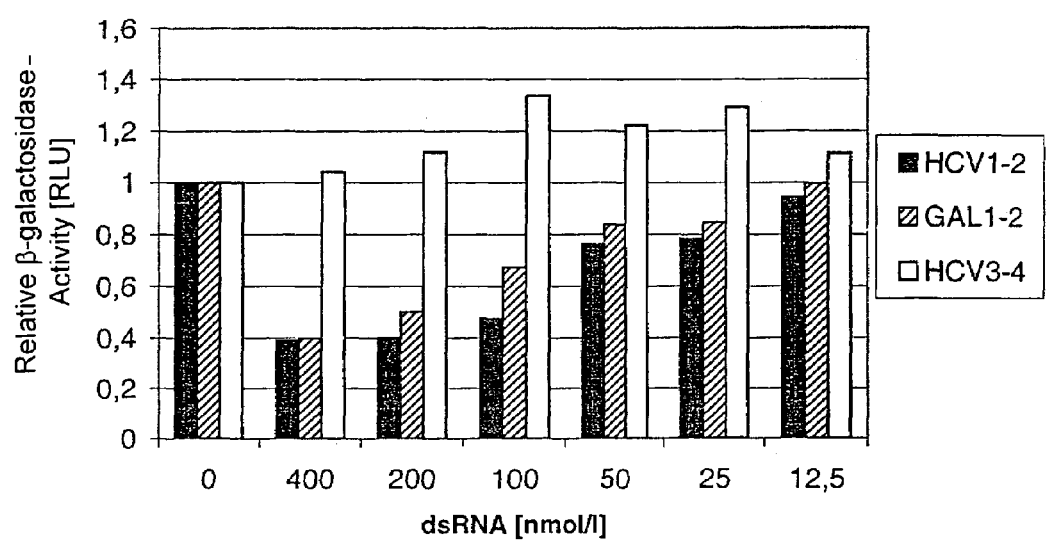
FIG. 8 shows the effect of various concentrations of HCV1-2, GAL1-2, and HCV3-4 dsRNAs on the activity of β-galactosidase expressed by means of the p2 plasmid.

2, GAL1-2, and HCV3-4 on the activity of β-galactosidase expressed by means of the p3 plasmid.

DETAILED DESCRIPTION OF THE INVENTION

The present invention discloses double-stranded ribonucleic acid (dsRNA), as well as compositions and methods for inhibiting the replication of a (+) strand RNA virus, such as a Hepatitis C Virus (HCV), using the dsRNA. The present invention also discloses compositions and methods for treating diseases in organisms caused by infection with HCV or HCV-associated diseases. dsRNA directs the sequence-specific degradation of mRNA through a process known as RNA interference (RNAi). The process occurs in a wide variety of organisms, including mammals and other vertebrates. The dsRNA of the invention comprises an RNA strand (the complementary strand) having a region that is complementary to at least a portion of a 3'-untranslated region (3'UTR) of a (+) strand RNA virus. Using a cell-based assay, the present inventors have demonstrated that very low dosages of these dsRNA can specifically and efficiently mediate RNAi in mammalian cells, resulting in a significant reduction in the activity or level of RNA encoded by the HCV genome as compared to untreated control cells. The present invention encompasses these dsRNAs and compositions comprising dsRNA and their use for specifically inhibiting the activity or replication of a (+) strand RNA virus such as HCV. The use of these dsRNAs enables the targeted degradation of mRNAs of genes that are implicated in (+) RNA strand viral infections, including Hepatitis C. Thus, the methods and compositions of the present invention comprising these dsRNAs are useful for treating HCV and HCV-associated diseases.

The following detailed description discloses how to make and use the dsRNA and compositions containing dsRNA to inhibit the activity or replication of a (+) strand RNA virus, as well as compositions and methods for treating viral diseases. The pharmaceutical compositions of the present invention comprise a dsRNA having a complementary nucleotide sequence of less than 30 nucleotides in length, preferably less than 25 nucleotides in length, and most preferably 21 to 24 nucleotides in length, and which is substantially identical to at least a part of a 3'-UTR of a (+) strand RNA virus, together with a pharmaceutically acceptable carrier. The dsRNA is less than 30 nucleotides in length, preferably less than 25 nucleotides in length, and most preferably 21 to 24 nucleotides in length. The dsRNA may be blunt ended, or one end, preferably the 3'-end of the complementary (antisense) strand, may have a single-stranded nucleotide overhang of 1 to 3 nucleotides, preferably 2 nucleotides in length.

Accordingly, certain aspects of the present invention relate to pharmaceutical compositions comprising the dsRNA of the present invention together with a pharmaceutically acceptable carrier, methods of using the compositions to inhibit the activity or replication of (+) strand RNA viruses such as HCV, and methods of using the pharmaceutical compositions to treat Hepatitis C and HCV-associated diseases.

I. Definitions

For convenience, the meaning of certain terms and phrases used in the specification, examples, and appended claims, are provided below.

As used herein, the terms "3'-untranslated region" and "3'-UTR" refer to the conserved, non-coding region at the 3'-end of a viral genome. The 3'-UTR can be the entire non-coding region or a fragment thereof. As used herein, the term "highly conserved region" refers to a region of the viral genome that remains evolutionarily constant, i.e., a genomic region that has a very low mutation rate and thus shares significant sequence identity (>99%) between distinct viral genotypes.

The term "complementary RNA strand" (also referred to herein as the "antisense strand") refers to the strand of a dsRNA which is complementary to a 3'-UTR of a (+) strand RNA virus. As used herein, the term "complementary nucleotide sequence" refers to the region on the complementary RNA strand that is complementary to the 3'-UTR. "dsRNA" refers to a ribonucleic acid molecule having a duplex structure comprising two complementary and anti-parallel nucleic acid strands. Not all nucleotides of a dsRNA must exhibit Watson-Crick base pairs; the two RNA strands may be substantially complementary (i.e., having no more than one or two nucleotide mismatches). The maximum number of base pairs is the number of nucleotides in the shortest strand of the dsRNA. The RNA strands may have the same or a different number of nucleotides. Similarly, the complementary nucleotide sequence is less than 30, preferably less than 25, and most preferably 21 to 24 nucleotides in length. The dsRNA is also preferably less than 30, more preferably less than 25, and most preferably 21 to 24 nucleotides in length. Thus, the length of the dsRNA preferably corresponds to the length of the complementary nucleotide sequence. "Introducing into" means uptake or absorption in the cell, as is understood by those skilled in the art. Absorption or uptake of dsRNA can occur through cellular processes, or by auxiliary agents or devices. For example, for in vivo delivery, dsRNA can be injected into a tissue site or administered systemically. In vitro delivery includes methods known in the art such as electroporation and lipofection.

As used herein, a "nucleotide overhang" refers to the unpaired nucleotide or nucleotides that protrude from the duplex structure when a 3'-end of one RNA strand extends beyond the 5'-end of the other complementary strand, or vice versa. "Blunt" or "blunt end" means that the lengths of the two RNA strand are the same at that end of the dsRNA, and hence there is no nucleotide(s) protrusion (i.e., no nucleotide overhang).

As used herein and as known in the art, the term "identity" is the relationship between two or more polynucleotide sequences, as determined by comparing the sequences. Identity also means the degree of sequence relatedness between polynucleotide sequences, as determined by the match between strings of such sequences. Identity can be readily calculated (see, e.g., *Computation Molecular Biology*, Lesk, A. M., eds., Oxford University Press, New York (1998), and *Biocomputing: Informatics and Genome Projects*, Smith, D. W., ed., Academic Press, New York (1993), both of which are incorporated by reference herein). While there exist a number of methods to measure identity between two polynucleotide sequences, the term is well known to skilled artisans (see, e.g., *Sequence Analysis in Molecular Biology*, von Heinje, G., Academic Press (1987); and *Sequence Analysis Primer*, Gribskov., M. and Devereux, J., eds., M. Stockton Press, New York (1991)). Methods commonly employed to determine identity between sequences include, for example, those disclosed in Carillo, H., and Lipman, D., *SIAM J. Applied Math.*(1988) 48:1073. "Substantially identical," as used herein, means there is a very high degree of homology (preferably 100% sequence identity) between the sense strand of the dsRNA and the corresponding part of the target 3'-UTR of the viral genome.

However, dsRNA having greater than 90%, or 95% sequence identity may be used in the present invention, and thus sequence variations that might be expected due to genetic mutation, strain polymorphism, or evolutionary divergence can be tolerated. Although 100% identity is preferred, the dsRNA may contain single or multiple base-pair random mismatches between the RNA and the target 3'-UTR.

As used herein, the term "treatment" refers to the application or administration of a therapeutic agent to a patient, or application or administration of a therapeutic agent to an isolated tissue or cell line from a patient, who has a disorder, e.g., a disease or condition, a symptom of disease, or a predisposition toward a disease, with the purpose to cure, heal, alleviate, relieve, alter, remedy, ameliorate, improve, or affect the disease, the symptoms of disease, or the predisposition toward disease.

As used herein, a "pharmaceutical composition" comprises a pharmacologically effective amount of a dsRNA and a pharmaceutically acceptable carrier. As used herein, "pharmacologically effective amount," "therapeutically effective amount" or simply "effective amount" refers to that amount of an RNA effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier or diluent for administration of a therapeutic agent. Pharmaceutically acceptable carriers for therapeutic use are well known in the pharmaceutical art, and are described, for example, in *Remington's Pharmaceutical Sciences*, Mack Publishing Co. (A. R. Gennaro, ed. 1985), which is hereby incorporated by reference herein. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

As used herein, a "transformed cell" is a cell into which a dsRNA molecule has been introduced by means of recombinant DNA techniques.

II. Double-stranded Ribonucleic Acid (dsRNA)

In one embodiment, the invention relates to a double-stranded ribonucleic acid (dsRNA) having a nucleotide sequence which is substantially identical to at least a portion of a target 3'-UTR of a (+) strand RNA virus. The dsRNA comprises two RNA strands that are sufficiently complementary to hybridize to form the duplex structure. One strand of the dsRNA comprises the nucleotide sequence that is substantially identical to a portion of the target 3'-UTR (the "sense" strand), and the other strand (the "complementary" or "antisense" strand) comprises a sequence that is complementary to the 3'-UTR. Because of this complementarity, the complementary RNA strand is able to base-pair with the complementary region of the 3'-UTR, thus inducing a structural change within the target 3'-UTR. For example, the complementary region of the 3'-UTR may be cleaved (through RNA interference) and/or ligated to other nucleic acid molecules, thus resulting in degradation and/or insertion or deletion mutations. Binding between the complementary RNA strand and the target 3'-UTR can also induce a structural change in the secondary and/or tertiary structure of the 3'-UTR. Because this region is vital for viral replication, such structural changes can block or significantly inhibit replication. Moreover, due to the high sequence variability of the genome of (+) strand RNA viruses, particularly HCV, sdRNAs that target conserved regions of the 3'-UTR may have a significant impact over a wide range of viral genotypes. Thus, not only is the efficiency of inhibition of viral replication increased by targeting a highly conserved region of the 3'-UTR, but targeting such regions also enables the treatment of diverse patient populations.

The sequence that is complementary to the target 3'-UTR (i.e., the complementary nucleotide sequence) is less than 30 nucleotides, preferably less than 25 nucleotides, and most preferably 21 to 24 nucleotides in length. Similarly, the dsRNA may have less than 30 nucleotides, preferably less than 25 nucleotides, and most preferably 21 to 24 nucleotides in length. The dsRNA can be synthesized by standard methods known in the art, e.g., by use of an automated DNA synthesizer, such as are commercially available from Biosearch, Applied Biosystems, Inc. In specific embodiments, the dsRNA can comprise the sequence set forth in SEQ ID NOS:12 or 13, or a complement thereof. In a particular embodiment, the antisense (complementary) RNA strand comprises the sequence set forth in SEQ ID NO:5, and the sense RNA strand comprises the sequence set forth in SEQ ID NO:4.

In one embodiment, at least one end of the dsRNA is blunt. dsRNA with at least one blunt end show improved stability as compared to dsRNA having two nucleotide overhangs. dsRNA with at least one blunt end shows greater in vivo stability (i.e., is more resistant to degradation in the blood, plasma, and cells). However, dsRNAs having at least one nucleotide overhang have unexpectedly superior inhibitory properties than their blunt-ended counterparts. Moreover, the present inventors have discovered that the presence of only one nucleotide overhang strengthens the interference activity of the dsRNA, without effecting its overall stability. The stability, particularly plasma stability, can thus be adjusted in accordance with needs of the particular application. dsRNA having only one overhang has proven particularly effective in vivo (as well as in a variety of cells, and cell culture mediums), and are more stable than dsRNA having two blunt ends. The single-stranded nucleotide overhang may be 1 to 3, preferably two, nucleotides in length. Preferably, the single-stranded overhang is located at the 3'-end of the complementary (antisense) RNA strand. Such dsRNAs have improved stability and inhibitory activity, thus allowing administration at low dosages, i.e., less than 5 mg/kg body weight of the recipient per day. Preferably, the complementary strand of the dsRNA has a nucleotide overhang at the 3'-end, and the 5'-end is blunt.

III. Pharmaceutical Compositions Comprising dsRNA

In one embodiment, the invention relates to a pharmaceutical composition comprising a dsRNA, as described in the preceding section, and a pharmaceutically acceptable carrier, as described below. The pharmaceutical composition comprising the dsRNA is useful for treating an infection or disease associated with the activity or replication of a (+) strand RNA virus.

The pharmaceutical compositions of the present invention are administered in dosages sufficient to inhibit the activity or replication of a (+) strand RNA virus, such as HCV. The present inventors have found that compositions comprising the dsRNA of the invention can be administered at surprisingly low dosages. A maximum dosage of 5 mg dsRNA per kilogram body weight per day is sufficient to inhibit or completely suppress the activity or replication of the target virus.

In general, a suitable dose of dsRNA will be in the range of 0.01 to 5.0 milligrams per kilogram body weight of the recipient per day, preferably in the range of 0.1 to 2.5 milligrams per kilogram body weight of the recipient per day, more preferably in the range of 0.1 to 200 micrograms per kilogram body weight per day, and most preferably in the range of 0.1 to 100 micrograms per kilogram body weight per day. The pharmaceutical composition may be administered once daily, or the dsRNA may be administered as two, three, four, five, six or more sub-doses at appropriate intervals throughout the day. In that case, the dsRNA contained in each sub-dose must be correspondingly smaller in order to achieve the total daily dosage. The dosage unit can also be compounded for delivery over several days, e.g., using a conventional sustained release formulation which provides sustained release of the dsRNA over a several day period. Sustained release formulations are well known in the art. In this embodiment, the dosage unit contains a corresponding multiple of the daily dose.

The skilled artisan will appreciate that certain factors may influence the dosage and timing required to effectively treat a subject, including but not limited to the severity of the infection or disease, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual dsRNAs encompassed by the invention can be made using conventional methodologies or on the basis of in vivo testing using an appropriate animal model, as described elsewhere herein.

Advances in mouse genetics have generated a number of mouse models for the study of various human diseases. For example, mouse repositories can be found at The Jackson Laboratory, Charles River Laboratories, Taconic, Harlan, Mutant Mouse Regional Resource Centers (MMRRC) National Network and at the European Mouse Mutant Archive. Such models may be used for in vivo testing of dsRNA, as well as for determining a therapeutically effective dose.

The pharmaceutical compositions encompassed by the invention may be administered by any means known in the art including, but not limited to oral or parenteral routes, including intravenous, intramuscular, intraperitoneal, subcutaneous, transdermal, airway (aerosol), rectal, vaginal and topical (including buccal and sublingual) administration. In preferred embodiments, the pharmaceutical compositions are administered by intravenous or intraparenteral infusion or injection.

For oral administration, the dsRNAs useful in the invention will generally be provided in the form of tablets or capsules, as a powder or granules, or as an aqueous solution or suspension.

Tablets for oral use may include the active ingredients mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredients is mixed with water or an oil such as peanut oil, liquid paraffin or olive oil.

For intramuscular, intraperitoneal, subcutaneous and intravenous use, the pharmaceutical compositions of the invention will generally be provided in sterile aqueous solutions or suspensions, buffered to an appropriate pH and isotonicity. Suitable aqueous vehicles include Ringer's solution and isotonic sodium chloride. In a preferred embodiment, the carrier consists exclusively of an aqueous buffer. In this context, "exclusively" means no auxiliary agents or encapsulating substances are present which might affect or mediate uptake of dsRNA in the cells that harbor the virus. Such substances include, for example, micellar structures, such as liposomes or capsids, as described below. Surprisingly, the present inventors have discovered that compositions containing only naked dsRNA and a physiologically acceptable solvent are taken up by cells, where the dsRNA effectively inhibits replication of the virus. Although microinjection, lipofection, viruses, viroids, capsids, capsoids, or other auxiliary agents are required to introduce dsRNA into cell cultures, surprisingly these methods and agents are not necessary for uptake of dsRNA in vivo. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The pharmaceutical compositions useful according to the invention also include encapsulated formulations to protect the dsRNA against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811; PCT publication WO 91/06309; and European patent publication EP-A-43075, which are incorporated by reference herein.

Toxicity and therapeutic efficacy of dsRNAs can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred.

The data obtained from cell culture assays and animal studies can be used in formulation a range of dosage for use in humans. The dosage of compositions of the invention lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In addition to their administration individually or as a plurality, as discussed above, the dsRNAs useful according to the invention can be administered in combination with other known agents effective in treating viral infections and diseases. In any event, the administering physician can adjust the amount and timing of dsRNA administration on the basis of results observed using standard measures of efficacy known in the art or described herein.

For oral administration, the dsRNAs useful in the invention will generally be provided in the form of tablets or capsules, as a powder or granules, or as an aqueous solution or suspension.

IV. Methods for Treating Viral Infections and Diseases

In one embodiment, the invention relates to a method for treating a subject having an infection or a disease associated with the replication or activity of a (+) strand RNA virus having a 3'-UTR, such as HCV. In this embodiment, the dsRNA can act as novel therapeutic agents for inhibiting replication of the virus. The method comprises administering a pharmaceutical composition of the invention to the patient (e.g., human), such that viral replication is inhibited. Because of their high specificity, the dsRNAs of the present invention specifically target (+) strand RNA viruses having a 3'-UTR, as described above, and at surprisingly low dosages.

Examples of (+) strand RNA viruses which can be targeted for inhibition include, without limitation, picornaviruses, caliciviruses, nodaviruses, coronaviruses, arteriviruses, flaviviruses, and togaviruses. Examples of picornaviruses include enterovirus (poliovirus 1), rhinovirus (human rhinovirus 1A), hepatovirus (hepatitis A virus), cardiovirus (encephalomyocarditis virus), aphthovirus (foot-and-mouth disease virus O), and parechovirus (human echovirus 22). Examples of caliciviruses include vesiculovirus (swine vesicular exanthema virus), lagovirus (rabbit hemorrhagic disease virus), "Norwalk-like viruses" (Norwalk virus), "Sapporo-like viruses" (Sapporo virus), and "hepatitis E-like viruses" (hepatitis E virus). Betanodavirus (striped jack nervous necrosis virus) is the representative nodavirus. Coronaviruses include coronavirus (avian infections bronchitis virus) and torovirus (Beme virus). Arterivirus (equine arteritis virus) is the representative arteriviridus.

Togavirises include alphavirus (Sindbis virus) and rubivirus (Rubella virus). Finally, the flaviviruses include flavivirus (Yellow fever virus), pestivirus (bovine diarrhea virus), and hepacivirus (hepatitis C virus). In a preferred embodiment, the virus is hepacivirus, the hepatitis C virus. Although the foregoing list exemplifies vertebrate viruses, the present invention encompasses the compositions and methods for treating infections and diseases caused by any (+) strand RNA virus having a 3'-UTR, regardless of the host. For example, the invention encompasses the treatment of plant diseases caused by sequiviruses, comoviruses, potyviruses, sobemovirus, luteoviruses, tombusviruses, tobavirus, tobravirus, bromoviruses, and closteroviruses.

The pharmaceutical compositions encompassed by the invention may be administered by any means known in the art including, but not limited to oral or parenteral routes, including intravenous, intramuscular, intraperitoneal, subcutaneous, transdermal, airway (aerosol), rectal, vaginal and topical (including buccal and sublingual) administration. In preferred embodiments, the pharmaceutical compositions are administered by intravenous or intraparenteral infusion or injection.

V. Methods for Inhibiting Expression of a Target Gene

In yet another aspect, the invention relates to a method for inhibiting the replication or activity of a (+) strand RNA virus, such as HCV. The method comprises administering a composition of the invention to the host organism such that replication of the target virus is inhibited. The organism may be an animal or a plant. Because of their high specificity, the dsRNAs of the present invention specifically target (+) strand RNA viruses having a 3'-UTR, and at surprisingly low dosages. Compositions and methods for inhibiting the replication of a target virus using dsRNAs can be performed as described elsewhere herein.

In one embodiment, the method comprises administering a composition comprising a dsRNA, wherein the dsRNA comprises a nucleotide sequence which is complementary to at least a part of a 3'-UTR of a (+) strand RNA virus. When the organism to be treated is a mammal, such as a human, the composition may be administered by any means known in the art including, but not limited to oral or parenteral routes, including intravenous, intramuscular, intraperitoneal, subcutaneous, transdermal, airway (aerosol), rectal, vaginal and topical (including buccal and sublingual) administration. In preferred embodiments, the compositions are administered by intravenous or intraparenteral infusion or injection.

The methods for inhibiting viral replication can be applied to any (+) strand RNA virus, such as those described above Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1

Inhibition of the 3'-UTR of HCV

To study RNA interference and the action of antisense oligonucleotides in a nonpathogenic assay, Sequence No. 1 in the sequence protocol was cloned in front of a gene that codes for E. coli β-galactosidase. Sequence No. 1 corresponds to a sequence from a highly conserved region of the 3'-UTR of the HCV genome that is 24 nucleotides in length. After transfection of the 3'-UTR plasmid in human HuH-7 liver cells, the sequence was transcribed as a part of an mRNA that codes for β-galactosidase. The mRNA sequence that corresponds to the 3'UTR is therefore identical to the HCV genome sequence and was subsequently used as the target sequence.

Generation of p2 and p3 Reporter Plasmids

The E. coli β-galactosidase (β-gal) gene was isolated from the commercially available expression vector pβ-Gal control (BD Biosciences Clontech, Tullastr. 4, 69126 Heidelberg, Germany, Gene Accession No. U13186, Nucleotide 280-3429).

The HCV sequence is part of a fusion gene in the p2 plasmid. The HCV sequence is part of the open reading frame of the sequence that codes for β-galactosidase, so that the HCV sequence is also expressed as part of a fusion protein. FIG. 1 shows the relevant sequence segments of the p2 plasmid (Sequence No. 2 of the sequence protocol). The HCV sequence is shown in italics. The beginning of the β-Gal gene (including 6 nucleotides of the Kozak sequence in front of the ATG codon) is underlined. The N-terminal amino acid sequence of the HCV β-galactosidase fusion protein is listed under the DNA sequence.

The HCV sequence is also part of a fusion gene in the p3 plasmid. However, the HCV sequence is located outside of the open reading frame of the sequence that codes for β-galactosidase, so that the HCV sequence is not expressed as part of a fusion protein. FIG. 2 shows the relevant sequence segment of the p3 plasmid (Sequence No. 3 in the sequence protocol). The HCV sequence is shown in italics. The beginning of the β-Gal gene (including 6 nucleotides of the Kozak sequence in front of the ATG codon) is underlined. The N-terminal amino acid sequence of the expressed β-galactosidase is listed under the DNA sequence.

The fusion genes that were generated in this way were cloned into the commercially available pcDNA3.1 (+) expression plasmid (Invitrogen, Life Technologies, Karlsruhe Technology Part, Emmy Noether Str. 10, 76131 Karlsruhe, Germany; Catalogue No. V790-20). This plasmid contains a neomycin resistance gene and thus confers on the HuH-7 cells that are transfected with it resistance to the G418. HuH-7 cells selected in the presence of G418 therefore harbor a reporter plasmid that stably integrated into the cell's genome. The commercially available pGL3-ctrl plasmid (Promega GmbH, High Tech Park, Schildkrötstr. 15, 68199 Mannheim, Germany; Gene Accession No. U47296 was used as the control plasmid. It codes and expresses the "firefly luciferase" gene.

Synthesis and Preparation of dsRNAs

Oligoribonucleotides are synthesized with an RNA synthesizer (Expedite 8909, Applied Biosystems, Weiterstadt, Germany) and purified by High Pressure Liquid Chromatography (HPLC) using NucleoPac PA-100 columns, 9×250 mm (Dionex Corp.; low salt buffer: 20 mM Tris, 10 mM NaClO$_4$, pH 6.8, 10% acetonitrile; the high-salt buffer was: 20 mM Tris, 400 mM NaClO4, pH 6.8, 10% acetonitrile. flow rate: 3 ml/min). Formation of double stranded dsRNAs is then achieved by heating a stoichiometric mixture of the individual complementary strands (10 M) in 10 mM sodium phosphate buffer, pH 6.8, 100 mM NaCl, to 80-90° C., with subsequent slow cooling to room temperature over 6 hours.

In addition, dsRNA molecules with linkers may be produced by solid phase synthesis and addition of hexaethylene glycol as a non-nucleotide linker (D. Jeremy Williams, Kathleen B. Hall, Biochem. (1996) 35:14665-14670). A Hexaethylene glycol linker phosphoramidite (Chruachem Ltd, Todd Campus, West of Scotland Science Park, Acre Road, Glasgow, G20 OUA, Scotland, UK) is coupled to the support bound oligoribonucleotide employing the same synthetic cycle as for standard nucleoside phosphoramidites (Proligo Biochemie GmbH, Georg-Hyken-Str.14, Hamburg, Germany) but with prolonged coupling times. Incorporation of linker phosphoramidite is comparable to the incorporation of nucleoside phosphoramidites.

DsRNA Oligonucleotides

Three short double-stranded ribonucleic acids (dsRNA) were used for the RNA interference. These dsRNAs each consist of 2 short oligoribonucleotides that are complementary to each other over almost the entire sequence region. Two nucleotides have no base pairing at either of the 3'-ends of the oligoribonucleotides, and therefore form dsRNA overhangs.

The sequence of one of the oligoribonucleotides is identical to the mRNA target sequence. This oligoribonucleotide is therefore called the sense strand. The sequence of the other oligoribonucleotide is complementary to the mRNA target sequence. This oligoribonucleotide is therefore called the antisense strand.

The double-stranded oligoribonucleotide designated as HCV1-2 is shown in FIG. 3 and compared to the HCV sequence of the mRNA formed by means of the p2 and p3 plasmids. The nucleotides shown in capital letters correspond to the HCV sequence in the p2 and p3 plasmids. HCV1-2 consists of the HCV 1 sense strand and the HCV 2 antisense strand, whereby two nucleotides in each exhibit no base pairing at the 3'-ends of the strands. The sense strand (HCV 1) depicted in Sequence No. 4 in the sequence protocol exhibits almost the same nucleotide sequence as the HCV sequence of an mRNA formed by means of the p2 and p3 plasmids, respectively. Three nucleotides of the HCV sequence are missing at the 5'-end, and two nucleotides are present at the 3'-end that are not a component of the HCV sequence. The antisense strand (HCV 2) depicted in Sequence No. 5 in the sequence protocol is, except for the two nucleotides at the 3'-end, complementary to HCV 1, and therefore also to the HCV sequence of an mRNA formed by means of the p2 and p3 plasmids, respectively. The HCV sequence corresponds to a 3'-untranslated region of the HCV genome.

A dsRNA designated as GAL1-2 was used as the positive control. It is shown in FIG. 4 in contrast to an mRNA sequence (designated as mRNA in FIG. 4) that corresponds to the β-Gal gene of the p2 and p3 plasmids. GAL 1-2 consists of the Gal 1 sense strand and the Gal 2 antisense strand, whereas two nucleotides in each exhibit no base pairing at the 3'-ends of the strands. The sense strand (Gal 1) shown in Sequence No. 6 in the sequence protocol exhibits almost the same nucleotide sequence as the mRNA sequence that corresponds to the β-Gal gene. The antisense strand (Gal 2) shown in Sequence No. 7 in the sequence protocol is, except for the two nucleotides at the 3'-end, complementary to Gal 1, and therefore also to the mRNA sequence that corresponds to the β-Gal gene.

In one part of the experiment, a dsRNA designated as HCV3-4, which has no relationship to the genes expressed here, was used as the negative control (FIG. 5). HCV3-4 consists of the HCV 3 sense strand and the HCV 4 antisense strand, whereby two nucleotides in each exhibit no base pairing at the 3'-ends of the strands. The sense strand (HCV 3) shown in Sequence No. 8 of the sequence protocol exhibits almost no similarity to the mRNA formed by means of the p2 and p3 plasmids, and therefore has no relationship to the expressed genes. The antisense strand (HCV 4) shown in Sequence No. 9 in the sequence protocol is, except for the two nucleotides at the 3'-end, complementary to HCV 3 and therefore also has no relationship to the mRNA that is formed.

In another part of the experiment, a dsRNA designated as K22 was used as the negative control. It also exhibits no relationship to the gene expressed here (FIG. 6). The sequences of both oligoribonucleotides that form the dsRNA are shown in Sequence Nos. 10 and 11 in the sequence protocol.

Three 21-nucleotide-long DNA antisense oligoribonucleotides were used as phosphothioates in the experiments on antisense oligoribonucleotides. The oligoribonucleotides were obtained from Metabion GmbH, Lena-Christ Str. 44, 82152 Martinsried, Germany. They are here designated as HCVPTO1, HCVPTO2, and HCVPTO3. HCVPTO1 and HCVPTO2 are complementary to different regions of the HCV-mRNA sequence formed by means of the p3 plasmid. HCVPTO3 is the negative control without relationship to the target sequence. HCVPTO1, HCVPTO2, and HCVPTO3 are shown in FIG. 7 in contrast to the HCV-mRNA sequence. RNA interference assays were tested on the HuH-7 type liver cell line (Nakabayashi et al. 1982 which can be infected by HCV and is used routinely to culture these viruses. The cells were cultured in DMEM (Dulbecco's Modified Eagle Medium) with 10% fetal calf serum (FCS).

a) Experiments relating to RNA interference

Transfection

Prior to transfection, $2 \times 10^4$ cells per well of a 96-well cell culture plate were seeded. 3 μg p2 plasmid and p3 plasmid, respectively, were mixed with 1 μg pGL3-ctrl plasmid. 0.25 μg of this plasmid mixture was placed in each well for transfection. Approximately 24 hours after seeding the cells, the p2/pGL3-ctrl and p3/pGL3-ctrl reporter plasmids were transfected together with dsRNA in HuH-7. The quantity of transfected DNA per well was constant.

The dsRNA was added to the plasmid mixtures in decreasing concentrations of 400 nmol/l to 12.5 nmol/l (in relation to 110 μl total transfection volume). The initial concentration of the HCV1-2, GAL1-2, and nonspecific HCV3-4 dsRNAs in each stock solution was 20 μmol/l. The dsRNAs were diluted by mixing them stepwise with the same volume of annealing buffer (AB, 100 mmol/l NaCl, 20 mmol/l sodium phosphate, pH 6.8) to arrive at the end concentration.

For an end concentration of 400 nmol/l, 2.2 μl stock solution was used for a transfection volume of 110 μl per well, and 6.6 μl stock solution was used for a transfection volume of 330 μl per well, respectively. The dilution steps were produced as shown in Table 1.

TABLE 1

Production of dsRNA dilution steps

| Solution No. | Initial solution | Concentration of initial solution (μmol/l) | Quantity of initial solution (μl) | Quantity of added AB (μl) | End concentration * (nmol/l) |
|---|---|---|---|---|---|
| 1 | Stock solution | 20 | 14.0 | | 400 |
| 2 | Solution 1 | 10 | 7.0 | 7.0 | 200 |
| 3 | Solution 2 | 5 | 7.0 | 7.0 | 100 |
| 4 | Solution 3 | 2.5 | 7.0 | 7.0 | 50 |
| 5 | Solution 4 | 1.25 | 7.0 | 7.0 | 25 |
| 6 | Solution 5 | 0.62 | 7.0 | 7.0 | 12.5 |

* End concentration, using 6.6 μl of each solution to a transfection volume of 330 μl Plasmids and dsRNA were cotransfected. Gene Porter 2 (PeQLab, Carl Thiersch Str. 2B, 91052 Erlangen, Germany; Catalogue No. 13-T202007) was used as the transfection agent. Each cotransfection was repeated three times.

For 3 wells of the 96-well plates a mixture was made that consisted of 2.0 μl of a plasma mixture consisting of the p2 plasmid and the pGL3 control plasmid (0.3875 μg/μl; 3:1), 6.6 μl dsRNA (20, 10, 5, 2.5, 12.5, and 0.62 μmol/l, respectively), and 16.4 μl DNA diluent B (supplied together with Gene Porter 2, PeQLab). This mixture was mixed with a mixture consisting of 6.0 μl Gene Porter 2 and 19 μl serum-free medium. The total volume of the resultant mixture was 50 μl, of which 16.5 μl was added to each of $2 \times 10^4$ HuH-7 in 100 μl of medium. Then a mixture was made that consisted of 2.0 μl of a plasmid mixture consisting of the p3 plasmid and the pGL3 control plasmid (0.3875 μg/μl; 3:1), 6.6 μl dsRNA (20, 10, 5, 2.5, 12.5, and 0.62 μmol/l, respectively), and 16.4 μl DNA diluent B. This mixture was mixed with a mixture consisting of 6.0 μl Gene Porter 2 and 19 μl serum-free medium. The total volume of the resultant mixture was 50 μl, of which 16.5 μl was added to each of $2 \times 10^4$ HuH-7 in 100 μl of medium. The transfected cells were incubated at 37° C. and 5% $CO_2$. 35 μl of fresh medium was added to each well, and the cells were incubated for another 24 hours. The cells were then trypsinied Detection Methods Used The effect of dsRNA on the expression of the reporter genes was determined by quantifying the β-galactosidase and luciferase activity by means of chemoluminescence. For this, lysates were made using the Tropix Lysebuffer (Applied Biosystems, 850 Lincoln Centre Drive, Foster City, Calif. 944404; Catalogue No. BD100LP) in accordance with manufacturer's instructions.

To quantify β-galactosidase activity, 2 μl lysate was used per analysis, as well as the substrate Galacto Star (Applied Biosystems, Tropix; Catalogue No. BM100S), in accordance with manufacturer instructions. To quantify luciferase activity, 5 μl lysate was used per analysis, as well as the substrate Luciferin (Applied Biosystems, Tropix; Catalogue No. BM100L) in accordance with manufacturer instructions. Luminescence was measured in each case using the Berthold Sirius luminometer (Berthold Detection Systems GmbH, Bleichstr. 56-58, 75173 Pforzheim, Germany).

Results

Figure 9:
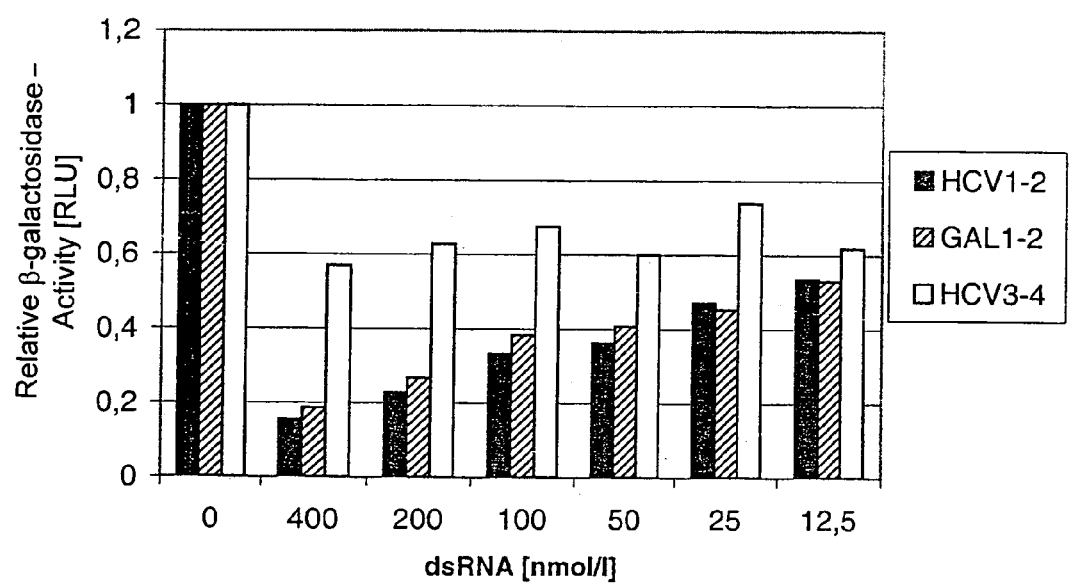
FIG. 9 shows the effect of various concentrations of HCV1-2, GAL-2, and HCV3-4 dsRNAs on the activity of β-galactosidase expressed by means of the p3 plasmid.

For each transfection assay, three 96-well plates were analyzed, such that in each case both β-galactosidase and luciferase were measured. The quotient of the relative light units (RLU) of β-galactosidase and the relative light units of luciferase were calculated. An average was determined for these three values. The average for p2/pGL3- and p3/pGL3 transfected cells without dsRNA, respectively, was arbitrarily defined as 1.0. The values that changed under the influence of dsRNA were recorded as a ratio to 1.0 (see FIGS. 8 and 9), i.e., a value of 0.6 corresponds to a 40% inhibition of β-galactosidase activity in comparison with untreated cells. In FIG. 8, cotransfection of sequence-specific dsRNA with the p2 plasmid resulted in a reduction in β-galactosidase activity. The HCV 1-2 and GAL 1-2 dsRNAs inhibit β-galactosidase with comparable effectiveness. At transfection volumes of 400 nmol/l and 200 mol/l of dsRNA, β-galactosidase activity decreases to 40% as compared to untreated cells. The inhibitory effect decreased with decreasing dsRNA concentration. The HCV3-4 control dsRNA leads to no decrease in β-galactosidase activity in lysate over the entire concentration range. A reduction in β-galactosidase expression is also detectable with cotransfection of the sequence-specific HCV1-2 dsRNA with the p3 plasmid (FIG. 9). HCV1-2 and GAL1-2 inhibit β-galactosidase activity with comparable effectiveness. At transfection volumes of 400 nmol/l and 200 mol/l of dsRNA, β-galactosidase activity decreases to approximately 20% as compared to untreated cells. The inhibitory effect decreased with decreasing dsRNA concentration. The HCV3-4 control dsRNA showed a weak inhibition of β-galactosidase activity to approximately 70% as compared to untreated cells. In the presence of the HCV1-2 dsRNA, both the p2 and p3 plasmids showed a marked decrease in β-galactosidase activity. Comparable effects were seen with the GAL1-2 dsRNA (positive control). The second control dsRNA, HCV3-4, led to no and markedly less inhibition of β-galactosidase activity, respectively. Expression and/or stability of RNA was markedly decreased by dsRNA in the experiments described. This was also true for HCV target sequences outside the open reading frame, which corresponds to the situation with the natural 3'-UTR region of HCV.

b) Experiments with antisense DNA oligonucleotides

To prepare for the experiments, p3 was stably transfected into HuH-7 cells using LipofectaminePLUS (GIBCO BRL Life Technologies, Karlsruhe Technology Park, Emmy Noether Str. 10, 76131 Karlsruhe, Germany). For this, 2×10⁴ cells were seeded per well of a 96-well cell culture plate. After 24 hours, the medium was replaced with 50 µl serum-free medium (DMEM). The transfection mixture consisted of 0.2 µg p3, 16.7 µl DMEM, 2 µl PLUS reagent, and 1 µl Lipofectamine reagent. Cells were transfected in accordance with manufacturer's instructions. After three hours, the transfection medium was replaced with 150 µl complete medium (DMEM+10% fetal calf serum). After 48 hours, the cells were transferred to wells in a 12-well cell culture plate, and cultured with 400 µg/ml G418 (Amersham Biosciences, Munzinger Str. 9, 79111 Freiberg, Germany). Colonies were collected and transferred to new wells in a 12-well cell culture plate. From these, the cells that grew in the new wells after 14-21 days were culled manually and cultured with 400 µg/ml G418 until the selection was comkplete. After approximately three manual selections, β-galactosidase activity was determined as described below by means of enzyme measurements. Then the number of cells that expressed galactosidase was determined using X-Gal staining. For this, the medium was aspirated and the cells were stained in the wells of a 96-well cell culture plate overnight in 100 µl X-Gal solution (10 mmol/l sodium phosphate, pH 7.0; 1 mmol/l MgCL₂; 150 mmol/l NaCl; 3.3 mmol/l K₄Fe(CN)₆*3H₂O; 3.3 mmol/l K₄Fe(CN)₆; 0,2% X-Gal) (X-Gal from PeQLab, Erlangen, Germany; all other chemicals from SIGMA, Grünwalder Weg 30, 82024 Taufkirchen, Germany). The best clone was designated "HuH-7 blue" and used for the experiments.

Transfection with dsRNA and Antisense DNA Oligonucleotides

To prepare for a transfection, 2×10⁴ cells of HuH-7 blue was seeded in 100 µl DMEM+10% FCS per well of a 96-well cell culture plate. After 24 hours, the dsRNA and the antisense DNA oligonucleotides were transfected. Fugene 6 (Roche Applied Sciences, Sandhofer Str. 116, 68305 Mannheim, Germany; Catalogue No. 1814443) was used for these transfections. Every fifth well containing HuH-7 blue cells was not treated. Stock solutions with a concentration of 20 µmol/l were made from the HCV 1-2, GAL1-2, and K22 dsRNAs. 1.6 µl of this stock solution was in each case mixed with 0.9 µl Fugene 6 and 108 µl DMEM. The dsRNA was therefore present at a concentration of 15 nmol/l. Each of 5 wells of a 96-well cell culture plate was transfected with 20 µl of this assay. Stock solutions were made with each of the antisense DNA oligonucleotides HCVPTO1, HCVPTO2, and HCVPTO3, and a concentration of 100 µmol/l. 1.2 µl of this stock solution was in each case mixed with 2.4 µl Fugene 6 and 108 µl DMEM. The dsRNA was therefore present in a concentration of 200 nmol/l. Each of 5 wells of a 96-well cell culture plate was transfected with 20 µl of this mixture.

Detection Methods

Figure 10:
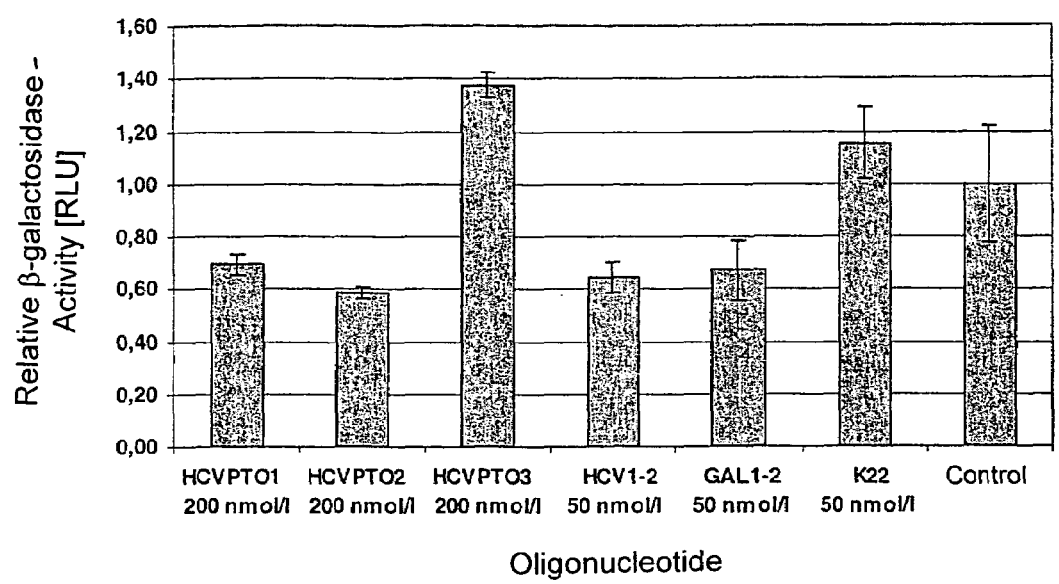
FIG. 10 shows the effect of the antisense oligonucleotides HCVPTO1, HCVPTO2, and HCVPTO3 of dsRNAs HCV1-

The effect of dsRNA oligonucleotides and antisense DNA oligonucleotides on the expression of reporter genes was determined by quantifying the β-galactosidase activity by means of chemoluminescence. For this, lysates were made using the Tropix Lysebuffer (Applied Biosystems, 850 Lincoln Centre Drive, Foster City, Calif. 944404; Catalogue No. BD100LP) in accordance with manufacturer's instructions. Chemoluminescence measurements were quantified as follows:

5 µl of lysate were placed in each reagent vessel and filled to 30 µl with β-Gal assay buffer (1 ml 1 mol/l sodium phosphate buffer, pH 8.0; 10 µl 1 mol/l MgCl₂, 10 µl 1.25 mg/ml Galakton [Tropix GC020, Applied Biosystems]; 9 ml deiodized water). Ml β-Gal stop mix (1 ml 2 mol/l NaOH, 250 µl 2.5% Emerald Enhancer [Applied Biosystems, Tropix, LAY250], 8.75 ml deionized water), mixed thoroughly, and immediately measured in the luminometer. If not otherwise noted, all reagents were supplied by SIGMA. Luminescence was measured in each case using the Berthold Sirius luminometer (Berthold Detection Systems GmbH, Bleichstr. 56-58, 75173 Pforzheim, Germany). 5 wells of a 96-well cell culture plate were analyzed per transfection assay. β-galactosidase activity was determined in each case, and the average of the 5 individual values was established. The average value for untransfected cells is arbitrarily defined as 1.0. The average values for transfected cells are then expressed as a ratio with the average for untransfected cells. For example, a value of 0.6 corresponds to an inhibition of β-galactosidase activity by 40% in comparison to untreated cells. The results are shown in FIG. 10.

Results

With transfection of sequence-specific antisense oligonucleotides (200 nmol/l) and dsRNA oligonucleotides (50 nmol/l) in the HuH-7 blue cell line, a reduction in β-galactosidase activity was detectable. HCVPTO1 reduced the activity of β-galactosidase by 35%, and HCVPTO2 by 40%. The HCVPTO3 oligonucleotide used as the negative control increased the activity by 40% as compared to untreated cells.

The HCV1-2 and GAL1-2 dsRNAs inhibited β-galactosidase activity with comparable effectiveness. β-galactosidase activity decreased by 37% in each case, as compared with untreated cells. The K22 nonspecific control increased activity by 15% in comparison with untreated cells.

Example 2

Treatment of a HCV Infected Patient with dsRNA

In this Example, HCV specific double stranded dsRNAs are injected into HCV infected patients and shown to specifically inhibit HCV gene expression.

dsRNA Administration and Dosage

The present example provides for pharmaceutical compositions for the treatment of human HCV infected patients comprising a therapeutically effective amount of a HCV specific dsRNA as disclosed herein, in combination with a pharmaceutically acceptable carrier or excipient. DsRNAs useful according to the invention may be formulated for oral or parenteral administration. The pharmaceutical compositions may be administered in any effective, convenient manner including, for instance, administration by topical, oral, anal, vaginal, intravenous, intraperitoneal, intramuscular, subcutaneous, intranasal or intradermal routes, among others. One of skill in the art can readily prepare dsRNAs for injection using such carriers that include, but are not limited to, saline, buffered saline, dextrose, water, glycerol, ethanol, and combinations thereof. Additional examples of suitable carriers are found in standard pharmaceutical texts, e.g. "Remington's Pharmaceutical Sciences", 16th edition, Mack Publishing Company, Easton, Pa., 1980.

Example 3

RNA Purification and Analysis

Efficacy of the dsRNA treatment is determined at defined intervals after the initiation of treatment using real time PCR on total RNA extracted from peripheral blood. Cytoplasmic RNA from whole blood, taken prior to and during treatment, is purified with the help of the RNeasy Kit (Qiagen, Hilden) and HCV mRNA levels are quantitated by real time RT-PCR.as described previously (Eder, M., et al., *Leukemia* (1999) 13:1383-1389; Scherr M et al., *BioTechniques*. (2001) 31:520-526).

Example 4

HCV-specific dsRNA Expression Vectors

HCV-specific dsRNA molecules that interact with HCV target RNA molecules and modulate HCV gene expression activity are expressed from transcription units inserted into DNA or RNA vectors (see, for example, Couture et A, 1996, TIG., 12, 5 1 0, Skillern et A, International PCT Publication No. WO 00/22113, Conrad, International PCT Publication No. WO 00/22114, and Conrad, U.S. Pat No. 6,054,299). These transgenes can be introduced as a linear construct, a circular plasmid, or a viral vector, which can be incorporated and inherited as a transgene integrated into the host genome. The transgene can also be constructed to permit it to be inherited as an extrachromosomal plasmid (Gassmann et al., 1995, Proc. Natl. Acad. Sci. USA 92:1292).

The individual strands of a dsRNA can be transcribed by promoters on two separate expression vectors and cotransfected into a target cell. Alternatively each individual strand of the dsRNA can be transcribed by promoters both of which are located on the same expression plasmid. In a preferred embodiment, the dsRNA is expressed as an inverted repeat joined by a linker polynucleotide sequence such that the dsRNA has a stem and loop structure.

The recombinant dsRNA expression vectors are preferably DNA plasmids or viral vectors. dsRNA expressing viral vectors can be constructed based on, but not limited to, adeno-associated virus (for a review, see Muzyczka et al. (1992, Curr. Topics in Micro.and Immunol. 158:97-129)), adenovirus (see, for example, Berkner et al. (1988, BioTechniques 6:616), Rosenfeld et al. (1991, Science 252:431-434), and Rosenfeld et al. (1992, Cell 68:143-155)), or alphavirus as well as others known in the art. Retroviruses have been used to introduce a variety of genes into many different cell types, including epithelial cells, in vitro and/or in vivo (see for example Eglitis, et al., 1985, Science 230:1395-1398; Danos and Mulligan, 1988, Proc. Natl. Acad. Sci. USA 85:6460-6464; Wilson et al., 1988, Proc. Natl. Acad. Sci. USA 85:3014-3018; Armentano et al., 1990, Proc. Natl. Acad. Sci. USA 87:61416145; Huber et al., 1991, Proc. Natl. Acad. Sci. USA 88:8039-8043; Ferry et al., 1991, Proc. Natl. Acad. Sci. USA 88:8377-8381; Chowdhury et al., 1991, Science 254:1802-1805; van Beusechem. et al., 1992, Proc. Nad. Acad. Sci. USA 89:7640-19; Kay et al., 1992, Human Gene Therapy 3:641-647; Dai et al., 1992, Proc. Natl. Acad. Sci. USA 89:10892-10895; Hwu et al., 1993, J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Recombinant retroviral vectors capable of transducing and expressing genes inserted into the genome of a cell can be produced by transfecting the recombinant retroviral genome into suitable packaging cell lines such as PA317 and Psi-CRIP (Comette et al., 1991, Human Gene Therapy 2:5-10; Cone et al., 1984, Proc. Natl. Acad. Sci. USA 81:6349). Recombinant adenoviral vectors can be used to infect a wide variety of cells and tissues in susceptible hosts (e.g., rat, hamster, dog, and chimpanzee) (Hsu et al., 1992, J. Infectious Disease, 166:769), and also have the advantage of not requiring mitotically active cells for infection.

The promoter driving dsRNA expression in either a DNA plasmid or viral vector of the invention may be a eukaryotic RNA polymerase I (e.g. ribosomal RNA promoter), RNA polymerase II (e.g. CMV early promoter or actin promoter or U1 snRNA promoter) or preferably RNA polymerase III promoter (e.g. U6 snRNA or 7SK RNA promoter) or a prokaryotic promoter, for example the T7 promoter, provided the expression plasmid also encodes T7 RNA polymerase required for transcription from a T7 promoter. The promoter can also direct transgene expression to the liver e.g albumin regulatory sequence (Pinkert et al., 1987, Genes Dev. 1:268276).

In addition, expression of the transgene can be precisely regulated, for example, by using an inducible regulatory sequence and expression systems such as a regulatory sequence that is sensitive to certain physiological regulators, e.g., circulating glucose levels, or hormones (Docherty et al., 1994, FASEB J. 8:20-24). Such inducible expression systems, suitable for the control of transgene expression in cells or in mammals include regulation by ecdysone, by estrogen, progesterone, tetracycline, chemical inducers of dimerization, and isopropyl-beta-D1-thiogalactopyranoside (EPTG). A person skilled in the art would be able to choose the appropriate regulatory/promoter sequence based on the intended use of the dsRNA transgene.

Preferably, recombinant vectors capable of expressing dsRNA molecules are delivered as described below, and persist in target cells. Alternatively, viral vectors can be used that provide for transient expression of dsRNA molecules. Such vectors can be repeatedly administered as necessary. Once expressed, the dsRNAs bind to target RNA and modulate its function or expression. Delivery of dsRNA expressing vectors can be systemic, such as by intravenous or intramuscular administration, by administration to target cells ex-planted from the patient followed by reintroduction into the patient, or by any other means that allows for introduction into a desired target cell.

DsRNA expression DNA plasmids are typically transfected into target cells as a complex with cationic lipid carriers (e.g. Oligofectamine) or non-cationic lipid-based carriers (e.g. Transit-TKO™). Multiple lipid transfections for dsRNA-mediated knockdowns targeting different regions of a single target gene or multiple target genes over a period of a week or more are also contemplated by the present invention. Successful introduction of the vectors of the invention into host cells can be monitored using various known methods. For example, transient transfection. can be signaled with a reporter, such as a fluorescent marker, such as Green Fluorescent Protein (GFP). Stable transfection. of ex vivo cells can be ensured using markers that provide the transfected cell with resistance to specific environmental factors (e.g., antibiotics and drugs), such as hygromycin B resistance.

The nucleic acid molecules of the invention described above can also be generally inserted into vectors and used as gene therapy vectors for human patients infected with HCV. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

We claim:

1. A method for inhibiting the replication of hepatitis C virus in a hepatitis C virus infected cell in vitro, which comprises introducing a double-stranded ribonucleic acid (dsRNA) into the cell, wherein the dsRNA comprises a sense RNA strand consisting of SEQ ID No. 4 and an antisense strand consisting of SEQ ID NO:5.

2. The method of claim 1, wherein the cell is a mammalian cell.

3. The method of claim 2, wherein the mammalian cell is a human cell.

* * * * *

SEQUENCE LISTING

<160> NUMBER OF SEQ ID NOS: 16

<210> SEQ ID NO 1
<211> LENGTH: 24
<212> TYPE: DNA
<213> ORGANISM: Artificial sequence
<220> FEATURE:
<223> OTHER INFORMATION: Synthetic oligonucleotide sequence that
      corresponds to a region of a genome

<400> SEQUENCE: 1
gtcacggcta gctgtgaaag gtcc                                          24

<210> SEQ ID NO 2
<211> LENGTH: 57
<212> TYPE: DNA
<213> ORGANISM: Artificial sequence
<220> FEATURE:
<223> OTHER INFORMATION: Synthetic oligonucleotide sequence
      corresponding to an artificial fusion gene

<400> SEQUENCE: 2
gtcaccatgt cgtcacggct agctgtgaaa ggtccagtca ccatgtcgtt tactttg      57

<210> SEQ ID NO 3
<211> LENGTH: 57
<212> TYPE: DNA
<213> ORGANISM: Artificial sequence
<220> FEATURE:
<223> OTHER INFORMATION: Synthetic oligonucleotide sequence
      corresponding to an artificial fusion gene

<400> SEQUENCE: 3
gtcaccttgt cgtcacggct agctgtgaaa ggtccagtca ccatgtcgtt tactttg      57

<210> SEQ ID NO 4
<211> LENGTH: 23
<212> TYPE: RNA
<213> ORGANISM: Artificial sequence
<220> FEATURE:

```
<223> OTHER INFORMATION: RNA sequence of sense strand of a synthetic
      dsRNA corresponding to Hepatitis C Virus

<400> SEQUENCE: 4
acggcuagcu gugaaagguc cgu                                                    23

<210> SEQ ID NO 5
<211> LENGTH: 23
<212> TYPE: RNA
<213> ORGANISM: Artificial sequence
<220> FEATURE:
<223> OTHER INFORMATION: RNA sequence of antisense strand of a synthetic
      dsRNA corresponding to Hepatitis C Virus

<400> SEQUENCE: 5
ggaccuuuca cagcuagccg uga                                                    23

<210> SEQ ID NO 6
<211> LENGTH: 23
<212> TYPE: RNA
<213> ORGANISM: Artificial sequence
<220> FEATURE:
<223> OTHER INFORMATION: RNA sequence of sense strand of a synthetic
      dsRNA corresponding to E. coli beta-galactosidase

<400> SEQUENCE: 6
gugaaauuau cgaugagcgu ggu                                                    23

<210> SEQ ID NO 7
<211> LENGTH: 23
<212> TYPE: RNA
<213> ORGANISM: Artificial sequence
<220> FEATURE:
<223> OTHER INFORMATION: RNA sequence of antisense strand of a synthetic
      dsRNA corresponding to E. coli beta-galactosidase

<400> SEQUENCE: 7
cacgcucauc gauaauuuca ccg                                                    23

<210> SEQ ID NO 8
<211> LENGTH: 21
<212> TYPE: RNA
<213> ORGANISM: Artificial sequence
<220> FEATURE:
<223> OTHER INFORMATION: RNA sequence of sense strand of a synthetic
      negative control dsRNA (no relationship to the expressed genes)

<400> SEQUENCE: 8
agacagucga cuucagccug g                                                      21

<210> SEQ ID NO 9
<211> LENGTH: 21
<212> TYPE: RNA
<213> ORGANISM: Artificial sequence
<220> FEATURE:
<223> OTHER INFORMATION: RNA sequence of the opposite strand of the
      synthetic negative control RNA of SEQ ID NO: 8 (no relationship
      to expressed genes)

<400> SEQUENCE: 9
aggcugaagu cgacugucug g                                                      21

<210> SEQ ID NO 10
<211> LENGTH: 24
<212> TYPE: RNA
<213> ORGANISM: Artificial sequence
<220> FEATURE:
```

```
<223> OTHER INFORMATION: RNA sequence of sense strand of a synthetic
      negative control dsRNA (no relationship to the expressed genes)

<400> SEQUENCE: 10
gaugaggauc guuucgcaug auug                                           24

<210> SEQ ID NO 11
<211> LENGTH: 24
<212> TYPE: RNA
<213> ORGANISM: Artificial sequence
<220> FEATURE:
<223> OTHER INFORMATION: RNA sequence of the opposite strand of the
      synthetic negative control RNA of SEQ ID NO: 10 (no relationship
      to expressed genes)

<400> SEQUENCE: 11
aucaugcgaa acgauccuca uccu                                           24

<210> SEQ ID NO 12
<211> LENGTH: 21
<212> TYPE: DNA
<213> ORGANISM: Artificial sequence
<220> FEATURE:
<223> OTHER INFORMATION: Antisense synthetic oligonucleotide -
      antisense to HCV sequence

<400> SEQUENCE: 12
ggacctttca cagctagccg t                                              21

<210> SEQ ID NO 13
<211> LENGTH: 21
<212> TYPE: DNA
<213> ORGANISM: Artificial sequence
<220> FEATURE:
<223> OTHER INFORMATION: Antisense synthetic oligonucleotide -
      antisense to HCV sequence

<400> SEQUENCE: 13
cctttcacag ctagccgtga c                                              21

<210> SEQ ID NO 14
<211> LENGTH: 21
<212> TYPE: DNA
<213> ORGANISM: Artificial sequence
<220> FEATURE:
<223> OTHER INFORMATION: Antisense oligonucleotide - antisense to HCV
      sequence

<400> SEQUENCE: 14
tgccgatcga cactttccag g                                              21

<210> SEQ ID NO 15
<211> LENGTH: 28
<212> TYPE: RNA
<213> ORGANISM: Hepatitis C virus

<400> SEQUENCE: 15
ucgucacggc uagcugugaa agguccag                                       28

<210> SEQ ID NO 16
<211> LENGTH: 25
<212> TYPE: RNA
<213> ORGANISM: Artificial sequence
<220> FEATURE:
<223> OTHER INFORMATION: Synthetic mRNA corresponding to the E. coli
      beta-Gal gene
```

-continued

```
<400> SEQUENCE: 16
cggugaaauu aucgaugagc guggu                                          25
```